United States Patent [19]

Hooven

[11] Patent Number: 4,714,459

[45] Date of Patent: Dec. 22, 1987

[54] THREE STAGE INTRACRANIAL PRESSURE CONTROL VALVE

[75] Inventor: Michael D. Hooven, Miami, Fla.

[73] Assignee: Cordis Corporation, Miami, Fla.

[21] Appl. No.: 812,779

[22] Filed: Dec. 23, 1985

[51] Int. Cl.[4] .............................................. A61M 27/00
[52] U.S. Cl. ......................................... 604/9; 137/504;
  137/508; 604/247
[58] Field of Search ...................................... 604/8–10,
  604/247; 137/504, 508, 859

[56] References Cited

U.S. PATENT DOCUMENTS

| | | | |
|---|---|---|---|
| 28,722 | 6/1960 | Whitacker | 137/508 |
| 79,436 | 6/1868 | Bechtel | 137/508 |
| 1,139,455 | 5/1915 | Gase | 137/508 |
| 1,159,214 | 11/1915 | Gueux | 137/508 |
| 1,199,152 | 9/1916 | Bruce | 137/508 |
| 1,468,434 | 9/1923 | Zander | |
| 2,207,382 | 7/1940 | McNamara | 277/21 |
| 2,290,151 | 7/1942 | McCollum | 137/508 X |
| 2,684,081 | 7/1954 | Chace | 137/859 X |
| 2,960,109 | 11/1960 | Wilson | 137/859 X |
| 2,969,066 | 1/1961 | Holter et al. | 128/350 |
| 3,109,429 | 11/1963 | Schwartz | 128/350 |
| 3,233,610 | 2/1966 | Wade | 128/350 |
| 3,270,771 | 9/1966 | Morgan | 137/525.3 |
| 3,288,142 | 11/1966 | Hakim | 128/350 |
| 3,308,798 | 3/1967 | Snider | 123/119 |
| 3,492,996 | 2/1970 | Fountain | 128/350 |
| 3,566,875 | 3/1971 | Stoehr | 128/350 |
| 3,601,128 | 8/1971 | Hakim | 128/350 |
| 3,654,932 | 4/1972 | Newkirk et al. | 128/350 V |
| 3,674,050 | 7/1972 | Kuffer et al. | 137/536 |
| 3,683,929 | 8/1972 | Holter | 128/350 V |
| 3,756,243 | 9/1973 | Schulte | 128/350 V |
| 3,768,508 | 10/1973 | Schulte | 137/522 |
| 3,769,982 | 11/1973 | Schulte | 128/350 |
| 3,782,410 | 1/1974 | Steuby | 137/496 |
| 3,804,113 | 4/1974 | Garcea | 137/496 |
| 3,827,439 | 8/1974 | Schulte et al. | 128/350 |
| 3,886,948 | 6/1975 | Hakim et al. | 128/350 V |
| 3,889,687 | 6/1975 | Harris | 128/350 V |
| 3,901,245 | 8/1975 | Spitz et al. | 128/350 V |
| 3,924,635 | 12/1975 | Hakim | 128/350 V |
| 3,970,105 | 7/1976 | Pelton et al. | 137/498 |
| 3,985,140 | 10/1976 | Harris | 128/350 V |
| 3,991,768 | 11/1976 | Portnoy | 128/350 |
| 3,999,553 | 12/1976 | Spitz | 128/350 |
| 4,103,689 | 8/1978 | Leighton | 128/350 V |
| 4,106,510 | 8/1978 | Hakim et al. | 128/350 V |
| 4,156,422 | 5/1979 | Hildebrandt et al. | 128/748 |
| 4,167,952 | 9/1979 | Reiniecke | 137/493 |
| 4,215,695 | 8/1980 | Spitz et al. | 128/350 |
| 4,246,930 | 1/1981 | Bishop | 137/493.9 |
| 4,332,255 | 6/1982 | Hakim et al. | 128/350 |
| 4,340,038 | 7/1982 | McKean | 128/1.3 |
| 4,437,493 | 3/1984 | Okuda et al. | 138/45 |
| 4,443,214 | 4/1984 | Marion | 604/9 |
| 4,452,423 | 6/1984 | Bevlavi | 251/65 |
| 4,551,128 | 11/1985 | Harim et al. | 604/9 |
| 4,627,832 | 12/1986 | Hooven et al. | 604/247 X |

FOREIGN PATENT DOCUMENTS 68509 7/1981 Netherlands .

Primary Examiner—Dalton L. Truluck
Attorney, Agent, or Firm—Lockwood, Alex, FitzGibbon & Cummings

[57] ABSTRACT

An implantable valve for controlling the passage of cerebrospinal fluid (CSF) from a ventricle of the brain to a suitable drainage location in the body includes a movable diaphragm which positions a valve seat in response to the pressure differential between the inlet and outlet of the valve. The valve seat defines a fluid orifice. An improved valve stem, preferably of one-piece construction, and provided with a series of cooperating diverging and converging frusto-conical portions, extends through the orifice to provide four stages or conditions of fluid flow and pressure control in response to relative movement between the valve seat and stem. In a first stage or condition of operation of the valve, wherein the fluid pressure differential falls below a threshold level, fluid flow is prevented. In a second stage, sufficient fluid flow is permitted to maintain a first substantially constant predetermined differential pressure. In a third stage, fluid flow through the valve is maintained at a substantially constant rate, and in a fourth stage sufficient fluid flow is permitted to maintain a second substantially constant predetermined differential pressure.

2 Claims, 10 Drawing Figures

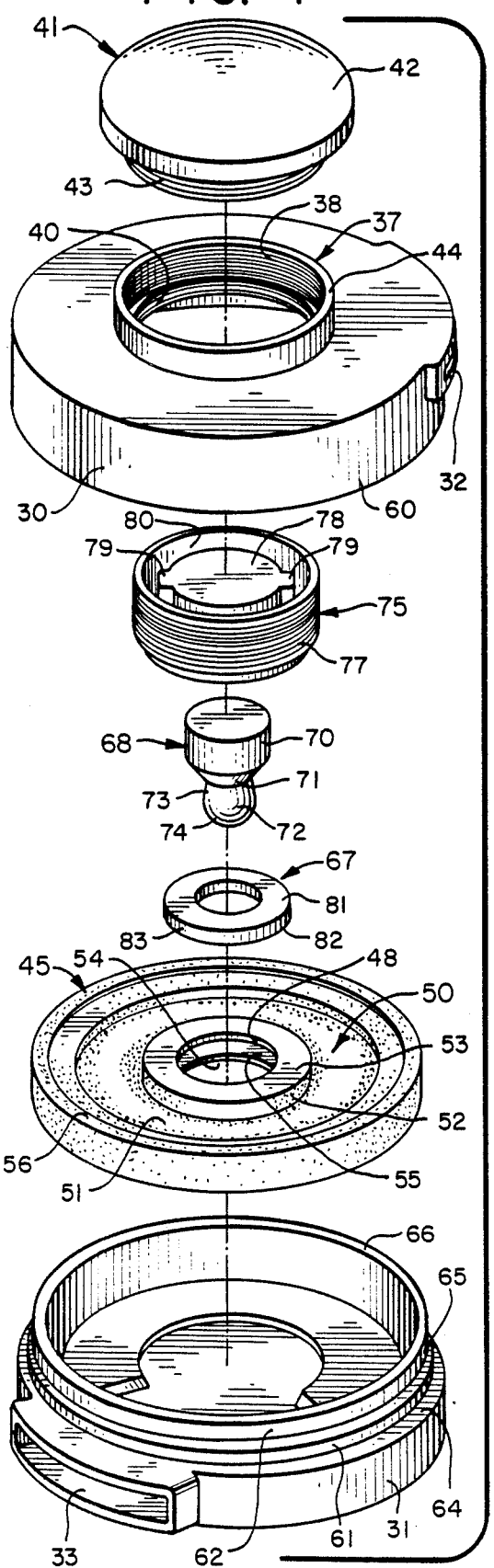
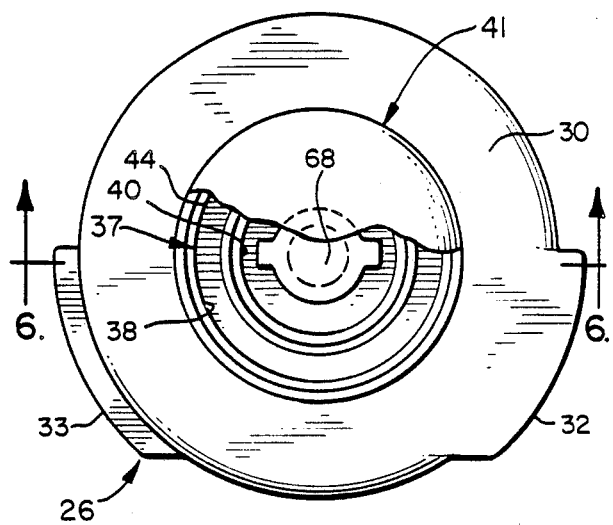
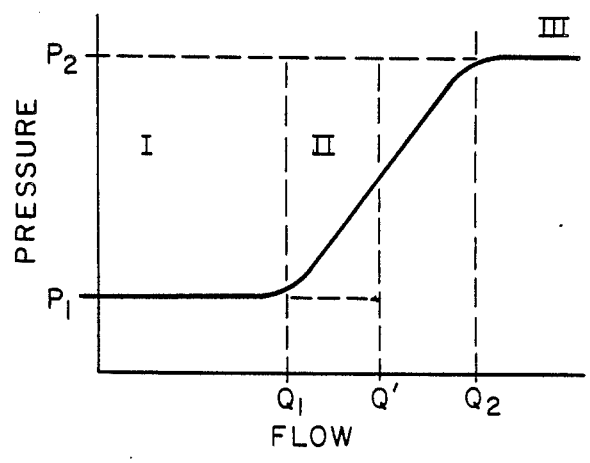

THREE STAGE INTRACRANIAL PRESSURE CONTROL VALVE

BACKGROUND OF THE INVENTION

The present invention relates to an intracranial pressure relief valve and, more particularly, to a single-piece combination valve stem and fluid flow restrictor for use in a three stage valve of the type which provides either constant pressure or constant flow characteristics in accordance with a fluid pressure differential applied across the valve.

Hydrocephalus is a condition in which the body, for any one of a variety of reasons, is unable to relieve itself of excess cerebrospinal fluid (CSF) collected in the ventricles of the brain. The excessive collection of the CSF in the ventricles results in an abnormal increase in both epidural and intradural pressures. This may in turn cause a number of adverse physiological effects including compression of brain tissue, impairment of blood flow in the brain tissue and impairment of the brain's normal metabolism.

Treatment of the hydrocephalic condition frequently involves relieving the abnormally high intracranial pressure. To this end, a variety of CSF pressure regulator valves and methods of controlling CSF pressure have been developed which include various check valves, servo valves or combinations thereof. Generally, such valves serve to divert CSF from the ventricles of the brain through a discharge line to some suitable drainage location in the body, such as the venous system or the peritoneal cavity. The check valves operate by opening when the difference between CSF pressure and pressure in the discharge line exceeds a predetermined level.

The use of a simple check valve in the treatment of hydrocephalus is potentially disadvantageous since it is possible for such a valve to open in response to a sudden, but nevertheless perfectly normal, increase in differential pressure between CSF in the ventricular spaces and fluid at the selected discharge location of the body, resulting in abnormal and potentially dangerous hyperdrainage of the ventricular spaces. For example, when a patient stands after lying in a recumbent position, the resulting increased vertical height of the fluid column existing between the head and the selected drainage location may result in such an increase in differential pressure. Accordingly, the valve described in the copending application of the present inventor, Ser. No. 672,868, abandoned in favor of Ser. No. 930,048, filed Nov. 12, 1986, has been developed which serves to prevent undesired hyperdrainage by limiting the flow rate of fluid through the valve when a sudden increase in differential pressure occurs.

In this valve, a diaphragm, movable in response to the pressure differential between ventricular CSF pressure and pressure of fluids at the drainage location of the body, included a valve seat movable with the diaphragm, such valve seat having a fluid metering orifice extending therethrough. The inner surface of the valve seat was provided with a precisely defined valving surface which in cooperation with a valve closing sphere or check valve, as well as a fluid flow restrictor, provided a three stage effect. By controlling the position of the sphere the valve seat and the restrictor as well as the configurations thereof, it was possible to establish four conditions of valve operation including three stages of controlled fluids flow. The first condition, not constituting a stage of fluid flow, included operation of the check valve against the valve seat to prevent fluid flow through the orifice. The second condition of operation, constituting the first stage of fluid flow, included movement of the diaphragm and valve seat away from the check valve or sphere in response to a first predetermined fluid pressure differential to permit limited flow of fluid through the orifice. The third condition, or second stage of fluid flow, occurred in response to sudden changes in fluid pressure differential such, as that resulting from a rather extreme change in physical position of the patient, with the result that the diaphragm moved further relative to the check valve and the restrictor entered the fluid flow orifice to become cooperatively effective with the valve seat to control fluid flow at a substantially constant rate thereby avoiding hyperdrainage. The fourth condition, or third stage of fluid flow, resulted from further movement of the diaphragm and valve seat relative to the restrictor to control further fluid under under conditions of a predetermined second substantially constant pressure differential.

A CSF pressure relief valve is typically miniaturized for implantation and is required to perform with a high degree of precision under highly demanding conditions throughout a rather extensive, ever-changing mode of operation. Consequently, it has been necessary to carefully control the dimensions of the various parts of the valve, particularly the valve seat, the valve stem assembly and the orifice defined by the valve seat. The parts involved are quite small, and working tolerances on the order of 0.0001 of an inch must be met. Considerable manufacturing costs may be incurred in constructing such a valve.

A CSF pressure relief valve incorporating a one piece valve stem is described in the copending application of the present inventor, Ser. No. 608,137, filed May 8, 1984, now U.S. Pat. No. 4,627,832, issued Dec. 9, 1986. The present invention is directed to an improvement in such a valve wherein the number of manufacturing steps, and hence the cost of the valve, is reduced. Basically, a valve constructed in accordance with the present invention is provided with a comparatively simply constructed valve seat, the inner surface of the seat which defines the fluid flow orifice not being primarily relied upon to establish the various conditions or stages of fluid flow, such conditions or stages being primarily dictated by a specially configured one-piece valve stem received in the orifice. The desirable flow characteristics are primarily governed by the shape of the valve stem or pin, with the valve seat merely defining the orifice and, in conjunction with the shape of the stem establishing the flow restriction characteristics as described.

In view of the foregoing, it is a general object of the present invention to provide a new and improved pressure regulator valve for relieving intracranial pressure caused by the presence of excess CSF in the ventricles of the brain.

It is a more specific object of the present invention to provide a pressure regulator valve which includes components which may be easily and economically manufactured.

It is a still more specific object of the present invention to provide a pressure regulator valve in which critically dimensioned components are of an easily manufactured configuration.

SUMMARY OF THE INVENTION

The invention is directed to a valve for controlling the passage of body fluids from one location in the body to another location. The valve includes a housing having first and second interior chambers. An inlet port establishes fluid communication between the first chamber and the one location, while an outlet port establishes fluid communication between the second chamber and the other location. A valving arrangement is located between the first and second chambers for regulating fluid flow between the same. This valving arrangement includes first and second parts and provides a first condition in which fluid flow between the first and second chambers is prevented, a second condition in which fluid flow batween the first and second chambers is sufficient to maintain a first substantially constant predetermined pressure in the first chamber, a third condition in which fluid flow between the first and second chambers is of a substantially constant rate, and a fourth condition in which fluid flow between the first and second chambers is sufficient to maintain a second substantially constant predetermined pressure in the first chamber. There is a partition means in the housing which carrier the first part of the valving mechanism, the partition separating the first and second chambers and being movable in response to the pressure differential therebetween. The second part of the valving mechanism is operatively associated with the first part such that the flow of fluid between the first and second chambers is sequentially conditioned by the parts from the first condition through the second and third conditions and to the fourth condition whereby, in response to an increasing pressure differential between fluid at the one location and fluid at the other location, the valve mechanism sequentially prevents the passage of fluid between the one location and the other location, maintains a constant fluid pressure differential between the one location and the other location, maintains a desired constant rate of fluid flow between the one location and the other location, and maintains a second constant fluid pressure differential between the one location and the other location.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 4 is an exploded perspective view of the pressure regulator valve showing the single piece valve stem and other principal elements of the valve.

FIG. 5 is a top plan view, partially in section, of the three stage pressure regulator valve shown in FIG. 4.

FIG. 10 is a graphical depiction of certain pressure and flow characteristics of the three stage pressure relief valve useful in understanding the operation thereof.

DESCRIPTION OF THE PREFERRED EMBODIMENT

Figure 1:
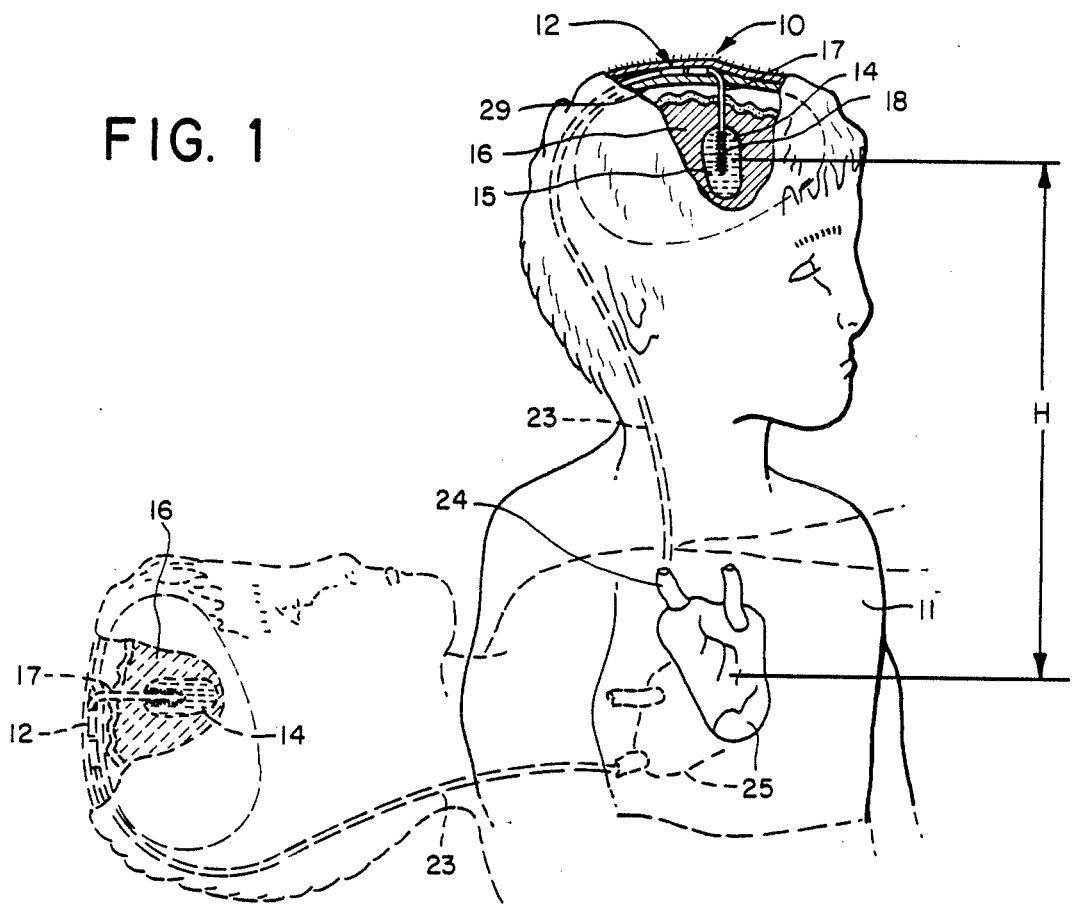
FIG. 1 is a perspective view, partially in section, of a CSF pressure relief system employing a three stage pressure regulator valve having a single piece valve stem constructed in accordance with the invention, showing such a system implanted within a patient.
Figure 2:
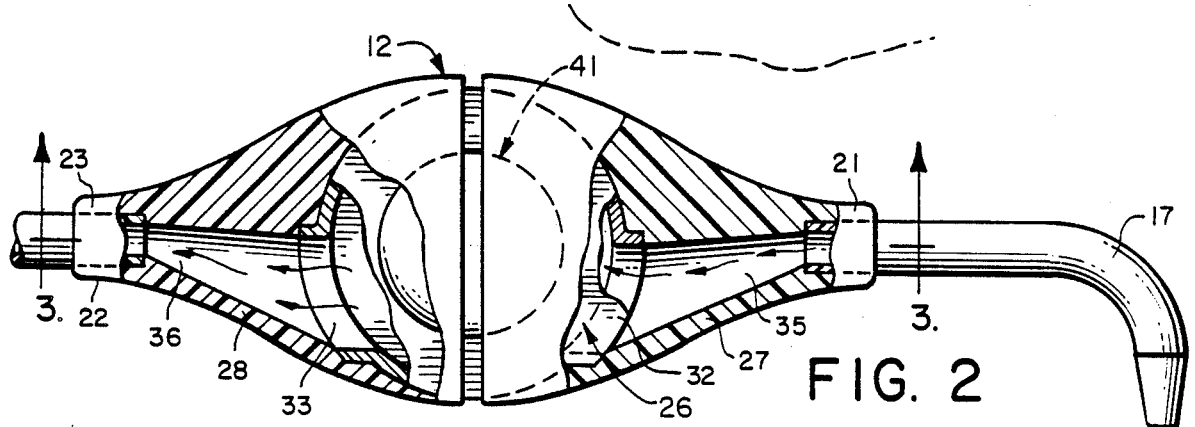
FIG. 2 is a plan view partially in section, of the pressure regulator valve showing the principal elements thereof.
Figure 3:
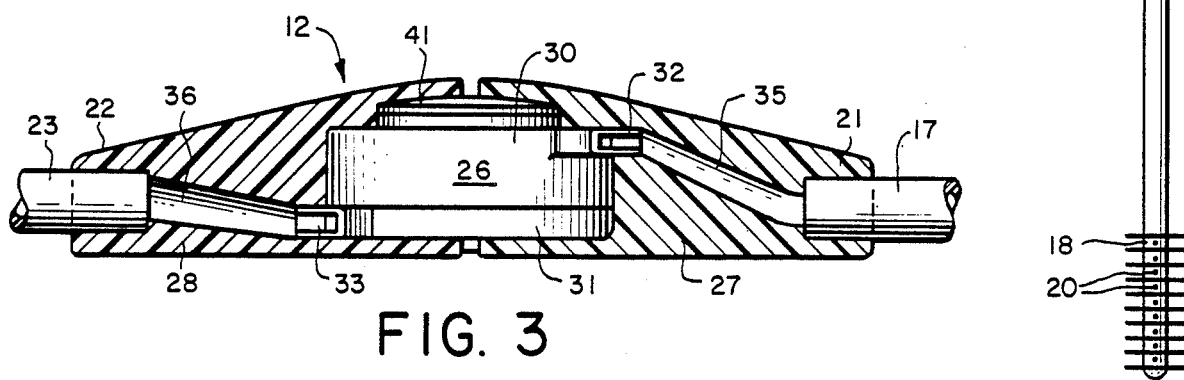
FIG. 3 is a cross-sectional view of the pressure regulator valve taken along line 3—3 of FIG. 2.

Referring to the drawings, and particularly to FIGS. 1-3, a CSF pressure relief system 10 for maintaining a desired predetermined intracranial pressure in a patient 11 is illustrated. The system shown includes a three stage pressure relief valve 12 constructed in accordance with the present invention for maintaining the desired intracranial pressure.

Cerebrospinal fluid (CSF) 14 is drained from a ventricle 15 of the brain 16 by means of a ventricular catheter 17. Preferably, the catheter is radio-opaque in order to facilitate its accurate placeaent with the brain. The distal end 18 of the catheter may be provided with a plurality of apertures 20 (FIG. 2) for allowing the passage of CSF therethrough and is positioned in a suitable brain ventricle as illustrated. The other end of the catheter is coupled to the inlet port 21 of the valve to establish fluid communication between the valve and the ventricle. The outlet port 22 of the valve is attached to one end of a drain catheter 23, the opposite end of which discharges into an appropriate location in the patient's body. A though the drain catheter is shown threaded through an appropriate vein 24 to terminate within the right atrium of the heart 25, a different drainage location, such as, for example, the peritoneal cavity, could be selected instead. When open, pressure relief valve 12 allows passage of CSF from the drain ventricle to the selected discharge location to relieve excessive intracranial pressure caused by excessive accumulation of CSF. Typically, pressure relief valve 12 includes means for adjusting the differential pressure threshold at which it opens so that the hydrocephalus pressure relief system can be adjusted to suit the specific requirements of an individual patient.

While an increased differential pressure may result from the excessive accumulation of CSF in the brain ventricle, such an increase might also be a perfectly normal response to ordinary physical activity of the patient. For example, when a patient stands after lying for some time in a recumbent position, as illustrated in phantom in FIG. 1, the differential pressure will suddenly increase by reason of the sudden increase in vertical height H of the fluid column existing between the distal end of the ventricular catheter and the drainage location. If the relief valve were to open and permit unrestrained fluid flow in response to this pressure increase, hyperdrainage of the ventricle, and a brain hematoma, are possible results. Accordingly, the valve increase means for preventing such unrestricted fluid flow to the drainage location in the event of a sudden increase in the differential pressure.

The internal construction and operation of the three stage valve may best be understood by reference to FIGS. 2-6. As illustrated, the valve includes a disc-shaped inner housing 26 fashioned from a durable, biologically compatible material, such as thermoplastic polymers of polyethersulfone or polycarbonates. The inner housing 26 is received within an outer housing comprising two members 27 and 28 formed of silicone rubber or a similar material bonded together over the inner housing. The dimensions of the inner and outer housings are selected so as to be compatible with subcutaneous implantation of the valve over the cranium 29 (FIG. 1).

As is best illustrated in FIGS. 3 and 4, the inner housing 26 comprises two circular cup-shaped housing members 30 and 31. Housing member 30 includes an inlet port 32, and housing member 31 includes an outlet port 33, by means of which fluid can pass to or from the interior region of the housing. In this regard, outer housing members 27 and 28 are provided with internal conduits 35 and 36, which provide fluid communication between inlet port 32, outlet port 33 and housing 26, respectively.

Upper housing member 30 is provided with an aperture 37 through the upper surface thereof. As illustrated in FIG. 4, the aperture 37 includes a region 38 of relatively larger diameter coaxially aligned above a region of relatively smaller diameter 40. Both the relatively larger diameter and smaller diameter regions of the aperture are internally threaded as illustrated in order to seal the aperture while still allowing ready access to the interior region of the housing, the upper housing member 30 includes a removable cap 41 having a domed upper surface 42 and an externally threaded cylindrical lower portion 43 dimensioned to engage the threads of region 38 of aperture 37. To provide a tight seal between the cap and the housing, the upper housing member may include a raised annular seat 44 adjacent the periphery of the aperture against which the cap bears as it is turned into the upper housing member.

Figure 6:
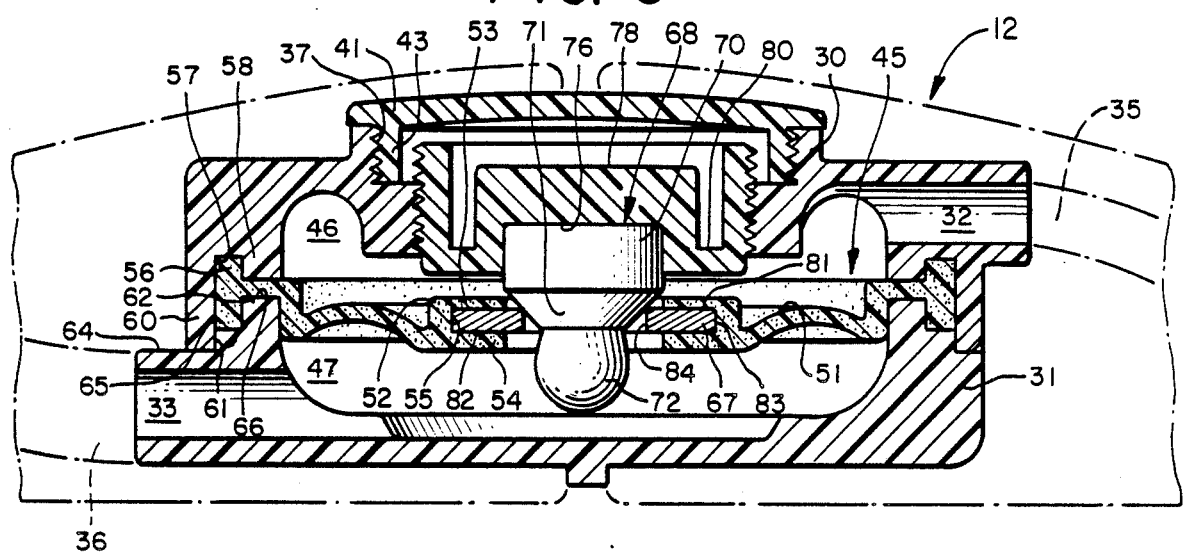
FIG. 6 is an enlarged cross-sectional view of the pressure regulator valve taken along lines 6—6 of FIG. 5.

Referring to FIGS. 4 and 6, pressure relief valve 12 includes partition means in the form of a diaphragm 45 which extends laterally across the interior region of the inner housing to provide that region into first and second interior chambers 46 and 47 (FIG. 6), respectively. The diaphragm 45 may be fashioned from a flexible biocompatible material, such as silicone rubber, and, as best seen in FIG. 4, may comprise a disc-shaped member having an aperture 48 provided centrally therethrough. The operative surface 50 of the diaphragm is provided with an annular groove 51 concentrically aligned with the center aperture which allows the operative surface to travel vertically in response to differential pressure across the diaphragm such as might result from a difference in pressures in the first and second interior chambers.

Toward its center, and in the region immediately surrounding the aperture, the thickness of the diaphragm 45 is increased to form a raised area 52, having upper and lower surfaces 53 and 54, respectively. An annular channel 55 of rectangular cross-section is provided in the sidewall of aperture 48 between surfaces 53 and 54. The diaphragm 45 also includes an integrally formed vertically projecting circular edge 56 projecting both above and below the operative surface 50 along its outer circumference. This edge facilitates installation of the diaphragm in the housing.

The manner in which the diaphragm is held in position relative to both the upper and lower housing members is best illustrated in FIGS. 4 and 6. The lower edge of the upper housing member is provided with a channel 57 thereby forming inner and outer sleeves 58 and 60, respectively. As illustrated, the vertical dimension of the inner sleeve 58 is less than that of the outer sleeve 60 while channel 57 is dimensioned to receive the outer edge portion 56 of the diaphragm. The upper edge surface of the lower housing member is provided with a pair of raised steps 61 and 62 which form concentric annular ledges 64, 65 and 66.

When assembled, the lower edge of the outer sleeve 60 contacts the first ledge 64, while the second ledge 65 is dimensioned so a to contact the outer edge portion 56 of the diaphragm when the diaphragm is in place. Similarly, the inner ledge 66 is dimensioned as to allow the diaphragm to be received in the space formed between the ledge and inner sleeve 58.

When assembled, upper housing member 30 interlocks with lower housing member 31 by engagement of their corresponding edges. Diaphragm 45 is received in the space provided therebetween with its periphery fixed relative to the two interior housing members. When mounted in this manner, the operative surface 50 of the diaphragm is free to travel vertically in response to a pressure differential existing between fluids contained in the first and second chambers.

To regulate the passage of fluid from the first chamber 46 to the second chamber 47, and hence from a brain ventricle to the drainage area of the body, the valve includes valving means for regulating fluid communication between the first and second chambers. These valving means, in accordance with the invention, take the form of a valve seat 67 mounted for movement with diaphragm 45, and a valve stem or pin 68 provided with variously related frusto-conical surfaces and being of single-piece cylindrical construction.

Referring in particular to FIGS. 4 and 6, the valve stem 68 includes a generally cylindrical upper mounting portion 70 of generally substantial axial extent as measured longitudinally of the stem, and of relatively large diameter as compared to the remaining portions of the stem 68. Below the enlarged cylindrical portion 70, the stem includes a frusto-conical portion 71 which provides an increasing diameter in an upwardly direction toward the cylindrical upper portion 70 of the stem 68, thus in reverse providing a converging frusto-conical area in a downwardly fluid flow direction toward the base of the stem 68. The ramped frusto-conical surface 71 just described performs multiple functions in the operation of the valve of the present invention in conjunction with the remaining elements of the valve means as will be described.

Still as viewed in FIGS. 4 and 6, the remaining portion 72 of the valve stem below the ramped area 71 constitutes in the downward fluid flow direction a diverging frusto-conical portion which is somewhat of a tear-drop shape. The portion or region 72 can best be described as consisting of two specific cylindrical areas, the first area 73 being basically frusto-conical and diverging in a downwardly direction along the axis of the stem 68, the remaining area 74 in the form illustrated being generally spherical although other forms, such as a flat bottom shape, can be utilized.

The single-piece valve stem 68 is positioned above and in coaxial alignment with the valve seat 67 and is held in position by means of a cylindrical collar 75 externally threaded and dimensioned to engage the threads of the relatively smaller diameter segment 40 of aperture 37. The collar 75 includes a central recess 76 (FIG. 6) dimensioned to receive the relatively larger diameter region 70 of the valve stem 68. The valve stem 68 and, specifically, the enlarged upper cylindrical region 70 thereof is fixedly mounted in the central recess 76 of the cylindrical collar 75, and this sub-assembly is threadedly received in the aperture 37 of the housing member 30. The top central portion of the collar 75 is in the form of a cylindrical dome 78 with oppositely spaced, laterally projecting ear-like lugs 79, the area between the dome 78 and the outer threaded portion of the collar 75 being in the form of an annular groove 80. With this arrangement, the cap 41 may be removed from the upper housing member 30 to gain access to the collar 75 to insert an appropriate tool in the groove 80 to engage the projecting ears 79 and rotate the collar 75 to raise or lower the valve stem, thereby providing very fine adjustment to the operational characteristics of the valve.

The valve seat 67, which may be formed of the same material as the single-piece valve step 68, is in the form of an annual disc-shaped member having flat, parallel, upper and lower faces or surfaces 81 and 82 (FIGS. 4 and 6), an outer vertical surface 83, and an inner vertical surface 84, such inner surface 84 being flat and vertically directed in an axial sense and defining the fluid flow orifice of the valve means. The valve seat 67 is received within the channel 55 formed in the raised segment 52 of the diaphragm 45. The central aperture or orifice 84 thus defined provides fluid communication between the first and second chambers 46 and 47. The diameter of the orifice is greater than that of the largest diameter of the lower portion of the valve stem 68 in the area where the downwardly diverging region 73 meets the spherical bottom portion 74 so as to permit the lower portion 72 of the valve stem 68 to pass through the fluid flow orifice as will be described. The diameter of the orifice 84 is less than the upper portion of the converging region 71 of the valve stem 68 and, of course, is less than the diameter of the upper cylindrical mounting portion 70 of the valve stem 68.

Figure 7:
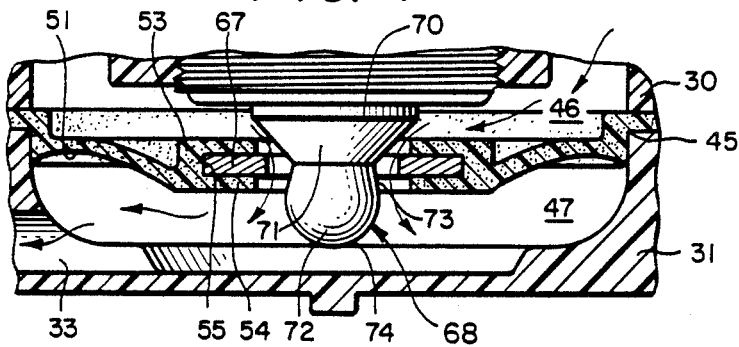
FIG. 7 is a cross-sectional view similar to FIG. 6, showing the pressure relief valve in a first constant pressure mode.

When no differential pressure acts on diaphragm 45, valve seat 67 contacts the frusto-conical ramp surface 71 of the valve stem 68 and the orifice 84 is totally occluded to prevent the passage of CSF between the first and second chambers. Downward travel of the diaphragm and the valve seat 67 progressively opens the orifice during the initial stages of such travel when the travel is occurring directly in relation to the converging frusto-conical ramp surface 71 of the valve stem. As further downward travel continues, such as shown in FIG. 7, the valve seat 67 becomes aligned laterally with the juncture of the converging ramp 71 and the diverging frusto-conical portion 73. By reason of the vertical definition of the orifice 84 by the valve seat 67, further downward movement of the valve seat along the lower diverging frusto-conical portion 73 of the valve stem results in fluid flow restriction and partial occlusion of the orifice between the first and second chambers. This is best shown in FIG. 8.

Figure 8:
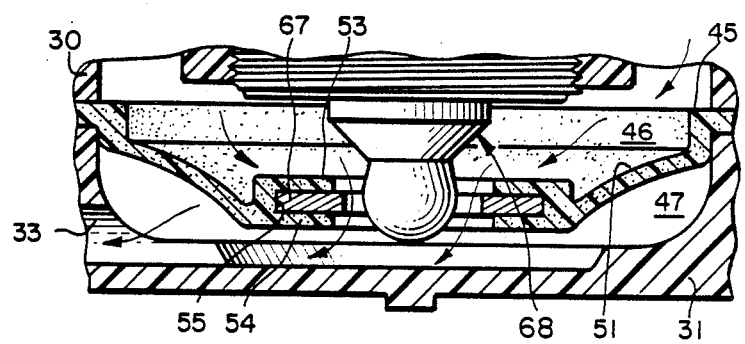
FIG. 8 is a cross-sectional view, similar to FIG. 6, showing the pressure relief valve in a constant flow-rate mode.
Figure 9:
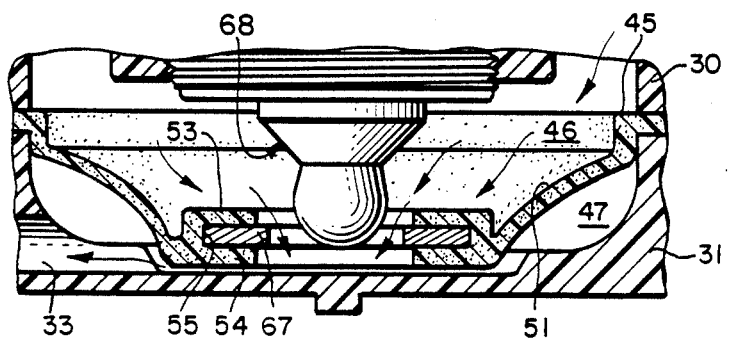
FIG. 9 is a cross-sectional view, similar to FIG. 6, showing the pressure relief valve in a second constant pressure mode.

The operation of the valve is illustrated in FIGS. 6–10. FIG. 6 illustrates the operation of the valve in the absence of applied CSF pressures. FIGS. 7-9 illustrate the operation of the valve in response to various levels of pressure versus flow characteristics of the valve.

Basically, the pressure relief valve 12 normally operates to maintain a predetermined differential pressure $P_1$ between fluids in the brain ventricles and at the selected discharge location of the body. The valve accomplishes this by adjusting the fluid flow rate Q so that the pressure $P_1$ is maintained. This operation of the valve is shown in Region I of FIG. 10.

When differential pressure rapidly increases, such as when the patient stands, a flow rate greater than a preselected rate $Q_1$ is necessary to maintain pressure $P_1$. However, such a flow rate may create the risk of undesirable hyperdrainage of the brain ventricle. Accordingly, when a rapid increase in differential pressure occurs, the valve automatically serves to maintain a relatively constant desired rate of fluid flow despite changes in differential pressure, as depicted in region II of FIG. 10. In a practical valve, the flow rate will not be entirely independent of the applied differential pressure but rather will increase from a lower flow rate $Q_1$ to a higher flow rate $Q_2$ as differential pressure increases between first pressure $P_1$ and a second pressure $P_2$, as indicated by the solid line in FIG. 10. Flow rates $Q_1$ and $Q_2$ are sufficiently low so that during a temporary rapid increase in differential pressure, pressure will return to normal before a quantity of CSF sufficient to cause adverse side effects may flow through the valve. In a typical valve $Q_1$ and $Q_2$ might be 0.4 ml./min. and 0.8 ml./min., respectively, while first and second pressures, $P_1$ and $P_2$, may have values of 80 and 350 millimeters of water, respectively.

While it is desirable to void high flow rates through the valve in order to avoid hyperdrainage of the ventricle, it may, under certain emergency conditions, be desirable to allow rapid shunting of CSF in order to avoid possible brain damage. When the valve is operating in region II, increases in differential pressure tend to close the valve between the first and second interior chambers. To avoid the possibility of building extremely high ventricular CSF pressure, the valve is constructed so that when differential pressure exceeds a predetermined pressure $P_2$ substantially higher than pressure $P_1$, the valve once again operates to allow a fluid flow rate sufficient to maintain a differential pressure no higher than pressure $P_2$. This operation is depicted in region III of FIG. 10. When the valve is operating in this region, further increases in differential pressure result in an increase in fluid flow through the valve thereby stabilizing differential pressure.

FIGS. 6–9 illustrate operation of the valve in the regions previously described. CSF applied to the inlet port 32 of the valve completely fills the first chamber 46 and exerts a downwardly directed force on the diaphragm 45 by reason of the CSF pressure within the brain ventricle. Since the second chamber 47 is in fluid communication with the selected drainage location in the body, the pressure of the CSF therein exerts an upwardly directed force on the lower surface of the diaphragm. Accordingly, the differential pressure between CSF in the brain ventricle and fluid at the drainage location results in ventricle deflection of both the diaphragm and the valve seat 67 rigidly attached thereto.

As shown in FIG. 6, when differential pressure is negative or non-existent, valve seat 67 contacts ramped surface 71 and the orifice 84 is totally occluded, thereby preventing CSF flow between chambers 46 and 47.

When the differential pressure is relatively low, such as when the valve is operating in region I of FIG. 10, the resulting slight downward displacement of the diaphragm is sufficient to displace the valve seat 67 relative to the valve stem 68 as shown in FIG. 7, thereby allowing CSF to pass through orifice 84 from chamber 46 to 47. While the downward deflection of the diaphragm is sufficient to allow the passage of CSF through the orifice, the divergence of the ramped region 73 of the valve stem 68 is not yet in sufficient lateral proximity to the inner surface of the valve seat 67 forming the orifice 84 so as to interfere with or restrict the flow of CSF between the chambers. Thus, the valve acts primarily as a constant pressure device whereby the pressure differential $P_1$ is maintained between the CSF in the chambers 46 and 47. A decrease in pressure in chamber 46 allows the diaphragm to move toward the orifice-occluding position of FIG. 6 to restrict flow between the chambers and cause pressure in chamber 46 to increase. It will be noted that the regulated pressure level $P_1$ in this mode can be adjusted by rotating collar 75 to vary the ventricle position of the valve stem 68 relative to the valve seat 67.

FIG. 8 illustrates the operation of the valve when a sudden increase in differential pressure is applied to the valve. When such an event occurs, the pressure differential exceeds the predetermined regulated pressure $P_1$ and the valve operates in region II of FIG. 10. The downward displacement of the diaphragm 45 is now sufficient to cause valve seat 67 to descend to the bottom extremity of the divergent ramped surface portion 73 of the valve stem 68 resulting in increased occlusion of the orifice 84. This primary restriction of fluid flow under the substantially increased pressure differential conditions described is in part largely due to the configuration of the valve seat 67 in the area of definition of the orifice 84, namely, the utilization of a flat and vertically directed inner surface defining such orifice. In effect, at this point of the operation of the valve, the valve seat 67 is functioning primarily as the restrictor while it is moving relative to the valve stem 68. The cooperating surface shapes of the valve seat 67 and functionally aligned tapered surface 73 of the valve stem 68 provide the necessary occlusion of the orifice to offset the higher fluid flow rate which would ordinarily result from the substantially and drastically increased differential pressure. As a result, fluid flow is sustained at a relatively uniform rate between the chambers despite the increase in differential pressure. Under these circumstances, the valve acts primarily as a constant flow device permitting the passage of fluid from chamber 46 to chamber 47 at a relatively constant, predetermined rate despite changes in applied differential pressure.

FIG. 9 illustrates operation of the valve in region III of FIG. 10, such as would occur when the differential pressure exceeds a predetermined pressure level $P_2$. In this condition, differential pressure displaces the diaphragm to a degree sufficient to cause the restricting action of the valve seat 67 to lessen by reason of the valve seat 67 moving further downwardly past the divergent end of the ramped surface 73 of the valve stem 68, thus allowing a greater fluid flow rate. The orifice 84 is now less restricted than in region II and when the valve is operating in this manner, increases in differential pressure allow a greater fluid flow rate. In this mode of operation the valve is functioning essentially as a constant pressure device whereby differential pressure greater than the predetermined maximum pressure $P_2$ is prevented.

The valve seat 67 and valve stem 68 may be formed of the same material and in the present invention the particular form of valve means described permits the use of a relatively thin valve seat 67 on the order, for example, of 0.003 inch. As miniaturization is of such great importance in connection with a valve of the type described, the thinness of the valve seat is significant. It can also be recognized that there is no critical taper or surface configuration forming a part of the valve seat 67, thus minimizing its cost of manufacture. The valve seat 67 provides a constant area restriction to fluid flow regardless of its positioning relative to valve stem 68. Any critical taper necessary for proper flow regulation forms a part of the valve stem 68 which is of comparatively larger size thus being relatively more readily manufactured. Still further, the particular frusto-conical surfaces formed on the valve stem 68 are more readily configured during manufacture as compared to critical configurations involving the evolution of spherical surfaces. The bottom semi-spherical surface portion 74 of the valve stem may be flattened if desired. Therefore, in all of its critical respects, the valve of the present invention is considerably easier and less costly to manufacture.

The valve stem 68 may be advantageously formed as a single-piece member from a hard bio-compatible material such as ruby, sapphire or the like. By reason of the threaded valve stem carrier 75, the valve stem 68 may be accurately positioned relative to the valve seat 67 and the other valve elements for optimum performance in a wide range of applications.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A subcutaneous implantable valve for regulating the flow of body fluids from one location in the body to another location, comprising:
   a housing having first and second interior chambers;
   inlet port means for establishing fluid communication between said first chamber and the one location;
   outlet port means for establishing fluid communication between said second chamber and the other location;
   a flexible diaphragm in said housing and dividing the same into said first and second chambers, said diaphragm being moveable in response to pressure differentials established between said first and second chambers;
   a relatively rigid valve seat mounted on said diaphragm for movement therewith, said valve seat being disc-shaped and centrally thereof defining an annular fluid flow passageway having an interior wall which is flat in an axial direction and which extends in the direction of fluid flow between said first and second chambers, said interior wall defining a first valving surface; and
   a one-piece valve stem of over-all generally cylindrical configuration mounted on said housing and projecting into said first interior chamber toward said second chamber and in coaxial alignment with said fluid flow passageway, said valve stem in the direction of fluid flow consisting of a cylindrical upper mounting portion of relatively substantial axial extent and having a relatively large diameter, said mounting portion having a substantial part thereof fixed in said housing to mount said valve stem thereon, said mounting portion in the direction of fluid flow merging with a first frusto-conical portion of decreasing diameter defining a second valving surface for engagement with said valve seat to establish a first condition of fluid flow whereby in the absence of fluid pressure differential fluid flow between said first and second chambers is prevented, said first portion in the direction of fluid flow merging with a second generally frusto-conical portion of increasing diameter defining a third valving surface cooperating with said second valving surface to coact with said first valving surface to establish a second condition of fluid flow wherein a first substantially constant predetermined pressure is maintained in said first chamber, and said second portion in the direction of fluid flow merging with a third generally spherical portion defining a fourth valving surface of progressively decreasing diameter cooperating with said third valving surface to coact with said first valving surface to establish a third condition of fluid flow wherein a substantially constant rate of fluid flow from said first chamber into said second chamber is maintained, said fourth valving surface further coacting with said first valving surface to establish a fourth condition of fluid flow wherein a second substantially constant predetermined pressure is maintained in said first chamber.

2. A regulating valve as defined in claim 1 wherein said housing includes a threadedly advancable and retractable member exposed externally of said housing for adjustable engagement, said upper mounting portion of said valve stem being engaged with said advancable and retractable member for adjustable movement of said valve stem in said housing relative to said valve seat.

* * * * *